US012742187B2

(12) United States Patent
Liao et al.

(10) Patent No.: US 12,742,187 B2
(45) **Date of Patent: *Sep. 22, 2026**

(54) METHOD FOR CONVERTING CARBON SOURCE INTO SERINE

(71) Applicant: NAN YA PLASTICS CORPORATION, Taipei (TW)

(72) Inventors: Te-Chao Liao, Taipei (TW); Jung-Jen Chuang, Taipei (TW); Yi-Cheng Li, Taipei (TW); Tzu-Huan Wong, Hualien County (TW); Liang-Jung Chien, Taipei (TW)

(73) Assignee: NAN YA PLASTICS CORPORATION, Taipei (TW)

( * ) Notice: Subject to any disclaimer, the term of this patent is extended or adjusted under 35 U.S.C. 154(b) by 266 days.

This patent is subject to a terminal disclaimer.

(21) Appl. No.: 18/632,419

(22) Filed: Apr. 11, 2024

(65) Prior Publication Data

US 2025/0215468 A1 Jul. 3, 2025

(30) Foreign Application Priority Data

Dec. 27, 2023 (TW) ................................ 112150902

(51) Int. Cl.

*C12P 13/06* (2006.01)
*C12N 9/04* (2006.01)
*C12N 9/10* (2006.01)
*C12N 9/16* (2006.01)

(52) U.S. Cl.

CPC ............ *C12P 13/06* (2013.01); *C12N 9/0006* (2013.01); *C12N 9/1096* (2013.01); *C12N 9/16* (2013.01); *C12Y 101/01095* (2013.01); *C12Y 206/01052* (2013.01); *C12Y 301/03003* (2013.01)

(58) Field of Classification Search

CPC ...................................................... C12P 13/06
See application file for complete search history.

(56) References Cited

U.S. PATENT DOCUMENTS

2016/0177353 A1 6/2016 Yu et al.

FOREIGN PATENT DOCUMENTS

JP 5948092 A 3/1984
JP 10248588 A 9/1998

OTHER PUBLICATIONS

Pengfei Gu, Fan Yang, Tianyuan Su, Fangfang Li, Yikui Li, Qingsheng Qi, "Construction of an I-serine producing *Escherichia coli* via metabolic engineering", J Ind Microbiol Biotechnol, 41, SIMB, 2014, pp. 1443-1450.

*Primary Examiner* — Suzanne M Noakes
(74) *Attorney, Agent, or Firm* — Li & Cai Intellectual Property (USA) Office

(57) ABSTRACT

A method for converting a carbon source into serine includes: synthesizing a DNA sequence; implanting the DNA sequence into a plasmid, so that the plasmid includes gene sequences of SEQ ID NO: 1, SEQ ID NO: 2, and SEQ ID NO: 3; implanting the plasmid into cyanobacteria through an electroporation treatment, so as to obtain modified cyanobacteria; and providing the carbon source to the modified cyanobacteria, so that the modified cyanobacteria convert the carbon source into the serine.

14 Claims, 3 Drawing Sheets

Specification includes a Sequence Listing.

METHOD FOR CONVERTING CARBON SOURCE INTO SERINE

CROSS-REFERENCE TO RELATED PATENT APPLICATION

This application claims the benefit of priority to Taiwan Patent Application No. 112150902, filed on Dec. 27, 2023. The entire content of the above identified application is incorporated herein by reference.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present disclosure relates to a method for converting a carbon source into serine, and more particularly to a method for converting a carbon source into serine by use of cyanobacteria.

BACKGROUND OF THE DISCLOSURE

Cyanobacteria are autotrophs that can synthesize the required nutrients by photosynthesis. Since the cyanobacteria have the ability to fix carbon dioxide into metabolites, the cyanobacteria are conventionally applied to production of alcohols and organic acids (e.g., ethanol, butanol, 2,3-butanediol, succinic acid, lactic acid, and isopropylene), so as to reduce the greenhouse effect and damages to the environment. However, the cyanobacteria lack the ability to convert a carbon source into serine, and thus cannot be applied to production of the serine in the conventional technology.

The serine can promote metabolism of fat and fatty acids, which is beneficial for maintaining the immune system and finds extensive use in medicine. The serine is conventionally and mainly produced by way of fermentation, proteolysis, and chemical synthesis, yet these ways of production still have numerous disadvantages and are limited in application. For example, glycine is used as the raw material for fermentation, and natural protein is used as the raw material for proteolysis. Since the product obtained in this manner is a mixture of different amino acids, purification and separation processes are further needed, thereby increasing the manufacturing costs. For chemical synthesis, the production costs are high, serious pollution may occur, and D-serine and L-serine that are simultaneously produced cannot be easily separated.

Therefore, how to use the cyanobacteria for converting the carbon source into the serine through improvements in manufacturing processes, so as to process carbon-containing waste gases and produce valuable chemicals at the same time, has become one of the important issues to be solved in the relevant industry.

SUMMARY OF THE DISCLOSURE

In response to the above-referenced technical inadequacies, the present disclosure provides a method for converting a carbon source into serine.

In order to solve the above-mentioned problems, one of the technical aspects adopted by the present disclosure is to provide a method for converting a carbon source into serine. The method includes: synthesizing a DNA sequence; implanting the DNA sequence into a plasmid, so that the plasmid includes gene sequences of SEQ ID NO: 1, SEQ ID NO: 2, and SEQ ID NO: 3; implanting the plasmid into cyanobacteria through an electroporation treatment, so as to obtain modified cyanobacteria; and providing the carbon source to the modified cyanobacteria, so that the modified cyanobacteria convert the carbon source into the serine.

In one of the possible or preferred embodiments, the plasmid is an *Escherichia coli* plasmid.

In one of the possible or preferred embodiments, the method further includes: implanting the plasmid into *Escherichia coli* for mass production.

In one of the possible or preferred embodiments, the cyanobacteria are *Synechococcus elongates*.

In one of the possible or preferred embodiments, the modified cyanobacteria are capable of producing 3-phosphoglycerate dehydrogenase, phosphoserine phosphatase, and phosphoserine aminotransferase.

In one of the possible or preferred embodiments, the electroporation treatment is to process for 2 msec to 10 msec at a voltage of between 0.5 kV and 1.5 kV.

In one of the possible or preferred embodiments, the electroporation treatment further includes adding polyethylene glycol having a concentration of between 0.5% and 2%.

In one of the possible or preferred embodiments, the serine is L-serine.

In one of the possible or preferred embodiments, the carbon source is carbon dioxide, glucose, sucrose, fructose, or galactose.

In order to solve the above-mentioned problems, another one of the technical aspects adopted by the present disclosure is to provide a method for converting a carbon source into serine, which includes using modified cyanobacteria to convert the carbon source into the serine. The modified cyanobacteria include gene sequences of SEQ ID NO: 1, SEQ ID NO: 2, and SEQ ID NO: 3.

In one of the possible or preferred embodiments, the serine is L-serine.

In one of the possible or preferred embodiments, the carbon source is carbon dioxide, glucose, sucrose, fructose, or galactose.

In one of the possible or preferred embodiments, the modified cyanobacteria convert the carbon source into glyceraldehyde 3-phosphate (G3P), and are capable of producing 3-phosphoglycerate dehydrogenase (SerA), so as to convert the glyceraldehyde 3-phosphate (G3P) into 3-phosphohydroxypyruvate (3P-HP).

In one of the possible or preferred embodiments, the modified cyanobacteria are capable of producing phosphoserine aminotransferase (SerC), so as to convert the 3-phosphohydroxypyruvate (3P-HP) into 3-phosphoserine (3P-serine).

In one of the possible or preferred embodiments, the modified cyanobacteria are capable of producing phosphoserine phosphatase (SerB), so as to convert the 3-phosphoserine (3P-serine) into the serine.

Therefore, in the method for converting the carbon source into the serine provided by the present disclosure, by virtue of "the modified cyanobacteria including gene sequences of SEQ ID NO: 1, SEQ ID NO: 2, and SEQ ID NO: 3" and "providing the carbon source to the modified cyanobacteria," the carbon source can be converted into the L-serine by use of the modified cyanobacteria. In this way, carbon reduction can be achieved, and valuable chemicals can be obtained at the same time.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The described embodiments may be better understood by reference to the following description and the accompanying drawings, in which.

DETAILED DESCRIPTION OF THE EXEMPLARY EMBODIMENTS

Figure 1:
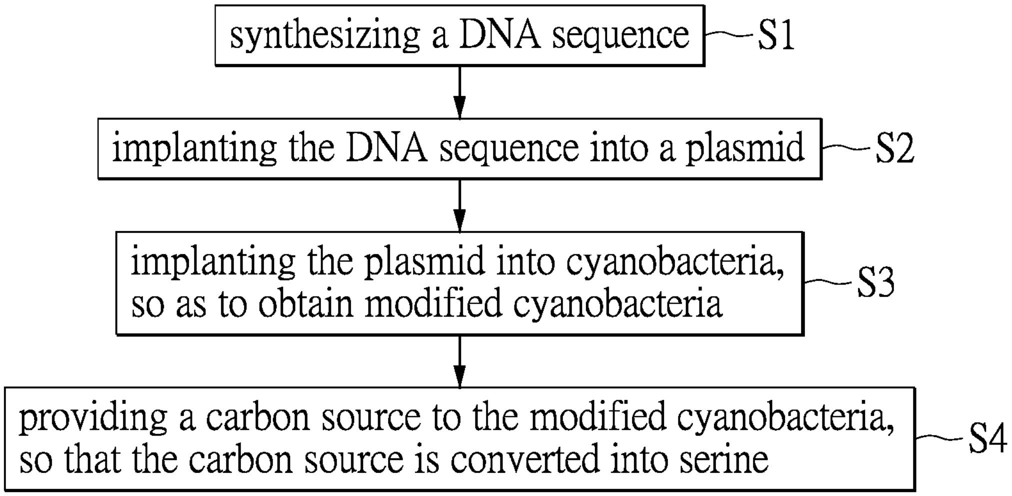
FIG. 1 is a flowchart of a method for converting a carbon source into serine according to the present disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a," "an" and "the" includes plural reference, and the meaning of "in" includes "in" and "on." Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first," "second" or "third" can be used to describe various components, signals or the like, which are for distinguishing one component/signal from another one only, and are not intended to, nor should be construed to impose any substantive limitations on the components, signals or the like.

It should be noted that, the term "or" recited in the present disclosure may include any one or a combination of relevant items listed herein according to practical requirements. Unless the context requires otherwise, the term "include", and variations such as "includes" and "including", will be understood to imply the inclusion of a stated integer or step or group of integers or steps, but not the exclusion of any other integer or step or group of integers or steps. In the present disclosure, the term "including" can be substituted with the term "containing" or "having".

The term "exogenous gene" recited in the present disclosure can also be referred to as "heterologous gene". The exogenous gene is not an endogenous genome that originates from a host cell or a target cell. Instead, the exogenous gene is taken from other species or cells, or from a synthetic gene or a nucleotide fragment, and is introduced into the host cell or the target cell by the genetic engineering technology.

Figure 2:
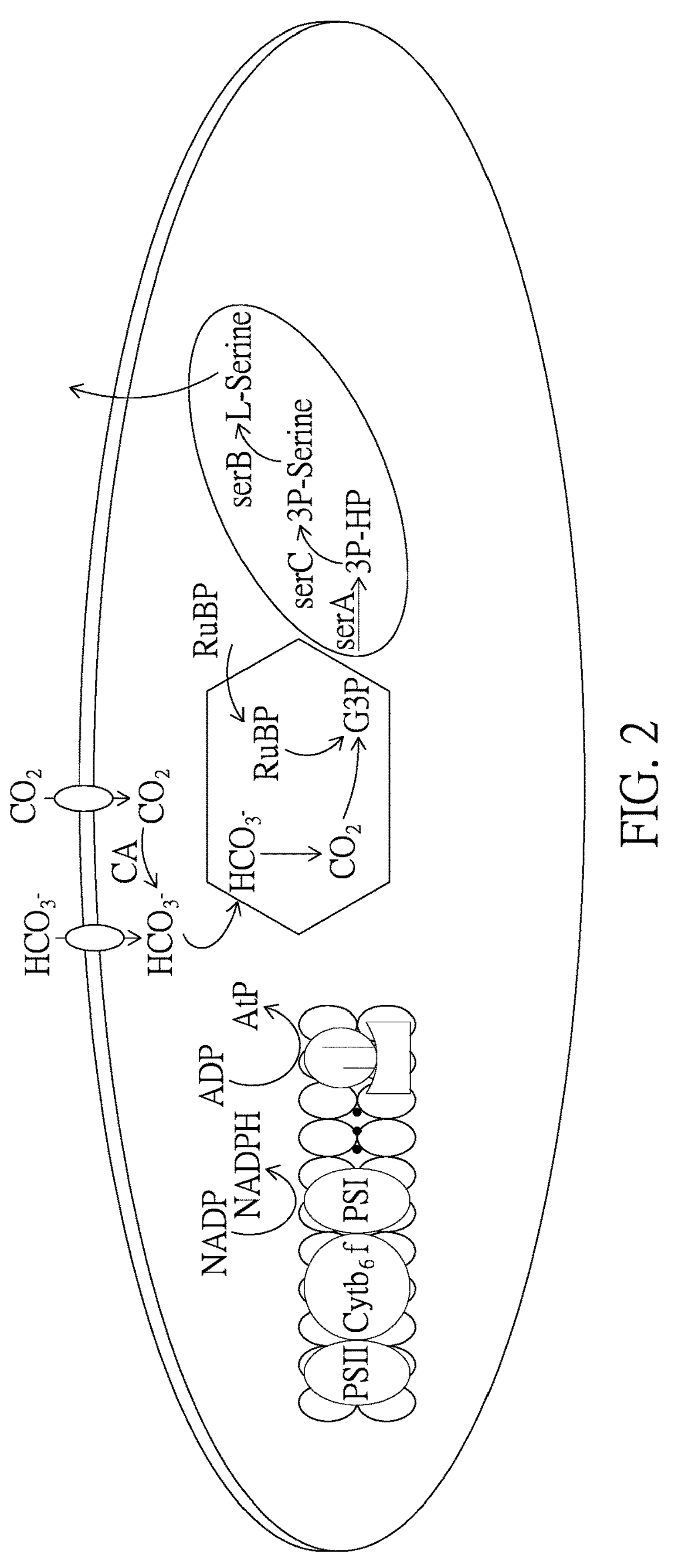
FIG. 2 is a schematic view showing a metabolic pathway of modified cyanobacteria according to the present disclosure.
Figure 3:
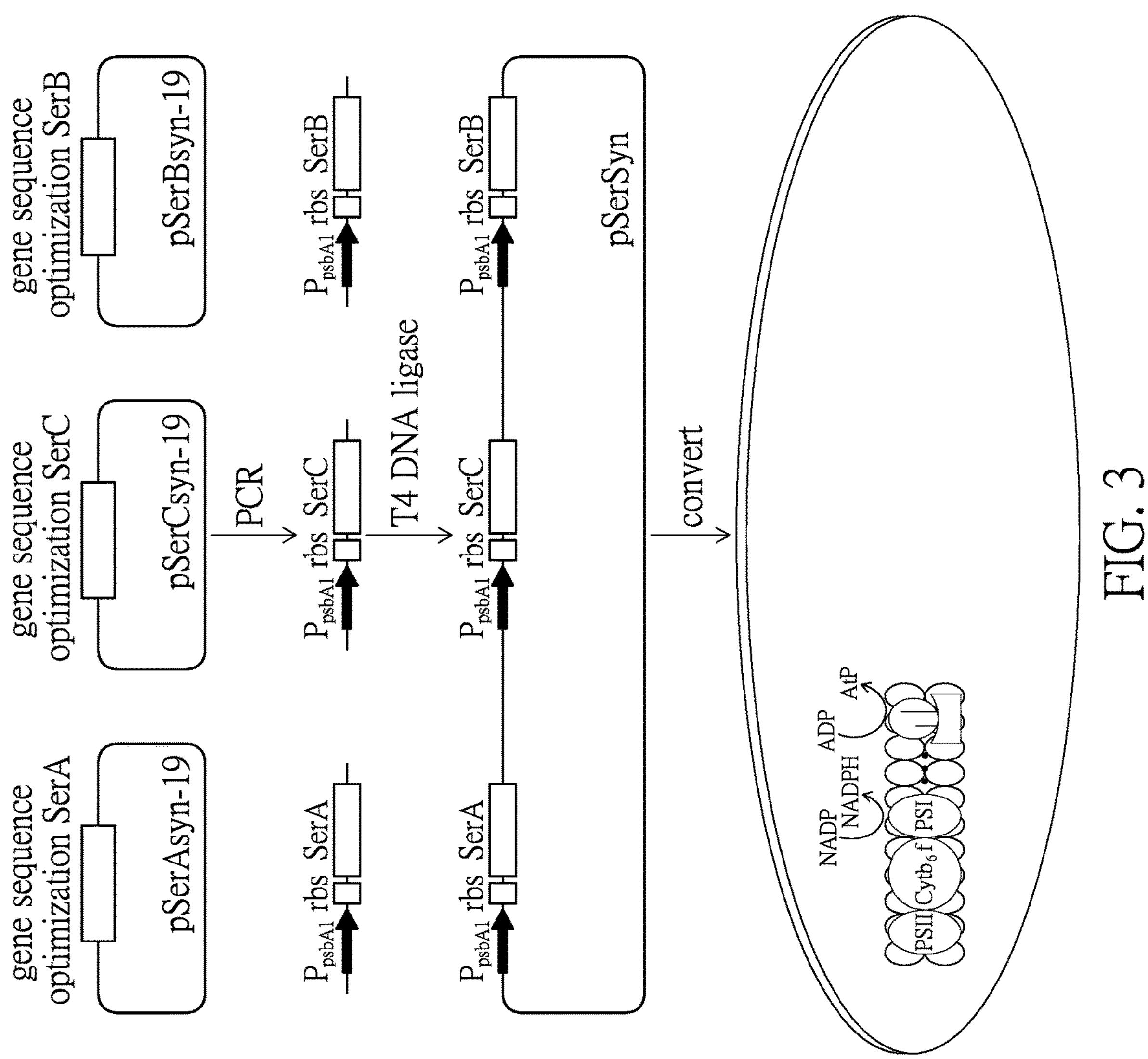
FIG. 3 is a schematic view showing construction of a plasmid according to the present disclosure.

Referring to FIG. 1 to FIG. 3, an embodiment of the present disclosure provides a method for converting a carbon source into serine. The method includes: synthesizing a DNA sequence (step S1); implanting the DNA sequence into a plasmid, so that the plasmid includes gene sequences of SEQ ID NO: 1, SEQ ID NO: 2, and SEQ ID NO: 3 (step S2); implanting the plasmid into cyanobacteria through an electroporation treatment, so as to obtain modified cyanobacteria (step S3); and providing the carbon source to the modified cyanobacteria, so that the modified cyanobacteria converts the carbon source into the serine (step S4).

In FIG. 2 and FIG. 3, NADP refers to nicotinamide adenine dinucleotide phosphate, NADPH refers to reduced nicotinamide adenine dinucleotide phosphate, ATP refers to adenosine triphosphate, ADP refers to adenosine diphosphate, PSII refers to photosystem II, PSI refers to photosystem I, Cytb$_6$f refers to cytochrome b$_6$f and is at a center of light-dependent reactions of oxygenic photosynthesis, RuBP refers to ribulose-1,5-bisphosphate, CA refers to carbonic anhydrases, and rbs refers to a ribosome binding site.

In the process of synthesizing the DNA sequence (step S1), the DNA sequence is synthesized to be suitable for genetic code recognition of the cyanobacteria, so that the cyanobacteria can recognize and produce corresponding substances. A genetic code that is suitable for genetic code recognition of *Synechococcus elongates* PCC7942 is particularly synthesized. Furthermore, the synthesized DNA sequence can be mass produced through a polymerase chain reaction (PCR). In one embodiment of the present disclosure, PCR conditions are as follows: repeating 30 cycles of denaturing at 98° C. for 30 seconds, denaturing at 98° C. for 10 seconds, low-temperature annealing at 56° C. for 20 seconds, and polymerizing at 72° C. for 45 seconds. Afterwards, PCR amplification is carried out under conditions of polymerizing at 72° C. for 10 minutes.

A plasmid DNA is massed produced and separated from native *Escherichia coli* DH5-alpha strains. In the process of implanting the DNA sequence into the plasmid (step S2), the designed DNA sequence is inserted into an *Escherichia coli* plasmid, so as to modify *Escherichia coli* for cloning and mass production. Accordingly, a recombinant plasmid is obtained and named as pSerSyn. However, the *Escherichia coli* cannot make use of carbon dioxide ($CO_2$). Even with the designed DNA sequence, the *Escherichia coli* is still not able to convert the carbon source into the serine. Hence, the plasmid DNA that is modified and massed produced needs to be taken out and transferred to native cyanobacteria.

Specifically, pSyn_1 can act as a backbone in construction of the plasmid used in the present disclosure, and carries the gene sequences of SEQ ID NO: 1, SEQ ID NO: 2, and SEQ ID NO: 3, so as to be integrated into and expressed in a genome of the cyanobacteria by homologous exchange. Then, an antibiotic is used to filter the modified cyanobacteria that have successfully obtained SEQ ID NO: 1, SEQ ID NO: 2, and SEQ ID NO: 3 after the homologous exchange. In other words, cyanobacteria strains that are successfully modified can grow on a solid medium containing the antibiotic.

In the process of implanting the plasmid into the cyanobacteria (step S3), the cyanobacteria are cultivated in a BG-11 medium, and a growth concentration of the strain is measured based on OD730 (optical density at 730 nm). More specifically, the plasmid is implanted into the cyanobacteria by electroporation, so as to obtain the modified cyanobacteria. In the process of electroporation, cells of the cyanobacteria are subjected to a high voltage and a low capacitance by application of an electric current within an extremely short period of time (ranging from microseconds to milliseconds), so that a potential difference in a cell membrane is formed, and changes occur to the structure of the cell membrane. As a result, the cell membrane is compressed and thinned, thereby generating numerous tiny holes. These tiny holes allow the plasmid to pass through the cell membrane and enter the cells of the cyanobacteria.

In order to achieve the optimal plasmid permeability effect, 0.5% to 2% (any concentration ranging between 0.5% and 2%) of polyethylene glycol (PEG) can be further added in this step. For example, the concentration can be 1.0% or 1.5%. Preferably, in the electroporation treatment, the cyanobacteria are processed for 2 msec to 10 msec at any voltage value ranging between 0.5 kV and 1.5 kV (e.g., 0.6 kV, 0.7 kV, 0.8 kV, 0.9 kV, 1.0 kV, 1.1 kV, 1.2 kV, 1.3 kV, and 1.4 kV). The processing time can be any millisecond within a range between 2 msec and 10 msec (e.g., 3 msec, 4 msec, 5 msec, 6 msec, 7 msec, 8 msec, and 9 msec). In the electroporation treatment, when a quantitative concentration of the native cyanobacteria is $1\times10^6$, amounts of the modified cyanobacteria strains that can be successfully obtained under different voltage and time conditions are further tested in the present disclosure (as shown in Table 1 below).

TABLE 1

(1% of PEG added in each group)

| Voltage (kV) | Time (msec) | Colony Count |
|---|---|---|
| 0.5 | 2 | 6 |
| 0.5 | 5 | 12 |
| 0.5 | 10 | 21 |
| 1.0 | 2 | 19 |
| 1.0 | 5 | 36 |
| 1.0 | 10 | 11 |
| 1.5 | 2 | 17 |
| 1.5 | 5 | 32 |
| 1.5 | 10 | 8 |

From the results of Table 1, when 1% of the PEG is added in the electroporation treatment of the present disclosure, the cyanobacteria are preferably processed for 10 msec at 0.5 kV, are more preferably processed for 5 msec at 1.5 kV, and are most preferably processed for 5 msec at 1.0 kV, so as to obtain a large colony count.

Generally, the native cyanobacteria are capable of reducing carbon dioxide to glyceraldehyde 3-phosphate (G3P). However, without relevant metabolic enzymes, the native cyanobacteria cannot continue metabolizing the glyceraldehyde 3-phosphate (G3P) into L-serine. In order to process the carbon source by use of the cyanobacteria and convert the carbon source into the serine, the modified cyanobacteria are prepared in the present disclosure.

In the present disclosure, the carbon source can be an industrial waste gas (i.e., a mixture of hydrogen, acetylene, methane, hydrogen sulfide, and acetaldehyde). Specifically, the mixture can include 30 ppm to 50 ppm of the hydrogen, 150 ppm to 250 ppm of the acetylene, 100 ppm to 200 ppm of the methane, 0.1 ppm to 1 ppm of the hydrogen sulfide, and 1 ppm to 5 ppm of the acetaldehyde. For example, the industrial gas can be a mixture of 40 ppm of the hydrogen ($H_2$), 200 ppm of the acetylene ($C_2H_2$), 150 ppm of the methane ($CH_4$), 0.5 ppm of the hydrogen sulfide ($H_2S$), and 3 ppm of the acetaldehyde ($CH_3CHO$).

In the process of providing the carbon source to the modified cyanobacteria (step S4), the modified cyanobacteria of the present disclosure are capable of producing 3-phosphoglycerate dehydrogenase (SerA), phosphoserine phosphatase (SerB), and phosphoserine aminotransferase (SerC), so as to independently carry out reactions of Formula 1 below and convert the glyceraldehyde 3-phosphate (G3P) into the L-serine.

Formula 1

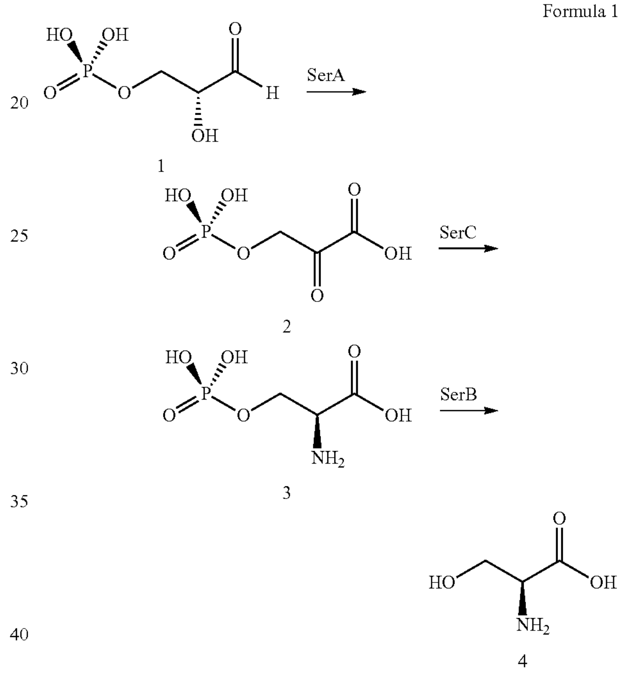

The modified cyanobacteria of the present disclosure have a plurality of exogenous genes, which include a nucleotide sequence encoded by a 3-phosphoglycerate dehydrogenase (SerA) gene, a nucleotide sequence encoded by a phosphoserine phosphatase (SerB) gene, and a nucleotide sequence encoded by a phosphoserine aminotransferase (SerC) gene. These genes can be expressed or overly expressed in the modified cyanobacteria. In other words, the modified cyanobacteria of the present disclosure have expression plasmids of SEQ ID NO: 1, SEQ ID NO: 2, and SEQ ID NO: 3.

Specifically, the modified cyanobacteria of the present disclosure still retain the property of the native cyanobacteria to convert the carbon source into the glyceraldehyde 3-phosphate (G3P). In addition, the modified cyanobacteria of the present disclosure are capable of producing the 3-phosphoglycerate dehydrogenase (SerA), so as to convert the glyceraldehyde 3-phosphate (G3P) into 3-phosphohydroxypyruvate (3P-HP). The modified cyanobacteria of the present disclosure are also capable of producing the phosphoserine aminotransferase (SerC), so as to convert the 3-phosphohydroxypyruvate (3P-HP) into 3-phosphoserine (3P-serine). The modified cyanobacteria of the present disclosure are further capable of producing the phosphoserine phosphatase (SerB), so as to convert the 3-phosphoserine (3P-serine) into the serine (especially the L-serine).

As such, the modified cyanobacteria of the present disclosure are capable of converting the carbon source into the L-serine and releasing the L-serine outside the cell. That is, the L-serine can be obtained without cell disruption. For example, the carbon source can be carbon dioxide, glucose, sucrose, fructose, or galactose. However, the present disclosure is not limited thereto. Preferably, the modified cyanobacteria of the present disclosure can make use of the carbon source in a carbon-containing industrial waste gas and convert the same into the L-serine. In this way, while the industrial waste gas is being processed by the modified cyanobacteria, valuable chemicals can also be obtained.

Another embodiment of the present disclosure further provides a method for converting a carbon source into serine, which at least includes using the modified cyanobacteria of the present disclosure to convert the carbon source into the serine. The modified cyanobacteria include the gene sequences of SEQ ID NO: 1, SEQ ID NO: 2, and SEQ ID NO: 3. In other words, the modified cyanobacteria have the expression plasmids of SEQ ID NO: 1, SEQ ID NO: 2, and SEQ ID NO: 3.

Accordingly, the modified cyanobacteria can convert the carbon source into the glyceraldehyde 3-phosphate (G3P). The cyanobacteria can use the sequence expressing SEQ ID NO: 1 to produce the 3-phosphoglycerate dehydrogenase (SerA), so as to convert the glyceraldehyde 3-phosphate (G3P) into the 3-phosphohydroxypyruvate (3P-HP). The cyanobacteria can also use the sequence expressing SEQ ID NO: 3 to produce the phosphoserine aminotransferase (SerC), so as to convert the 3-phosphohydroxypyruvate (3P-HP) into the 3-phosphoserine (3P-serine). The cyanobacteria can further use the sequence expressing SEQ ID NO: 2 to produce the phosphoserine phosphatase (SerB), so as to convert the 3-phosphoserine (3P-serine) into the serine.

Beneficial Effects of the Embodiments

In conclusion, in the method for converting the carbon source into the serine provided by the present disclosure, by virtue of "the modified cyanobacteria including gene sequences of SEQ ID NO: 1, SEQ ID NO: 2, and SEQ ID NO: 3" and "providing the carbon source to the modified cyanobacteria," the carbon source can be converted into the L-serine by use of the modified cyanobacteria. In this way, carbon reduction can be achieved, and valuable chemicals can be obtained at the same time.

Furthermore, the modified cyanobacteria strains used in the present disclosure include the gene sequences of SEQ ID NO: 1, SEQ ID NO: 2, and SEQ ID NO: 3, and can thus display the property of converting the carbon source into the serine. Specifically, by cultivating the modified cyanobacteria of the present disclosure in an environment of 38° C. with 3% of carbon dioxide ($CO_2$) and 25 mM of sodium bicarbonate ($NaHCO_3$) for 60 hours, as high as 2.78 g/L of the L-serine can be produced. Since the modified cyanobacteria of the present disclosure can only produce the L-serine, there is no need to separate D-serine and the L-serine. Compared with chemical synthesis, by using the modified cyanobacteria to convert the carbon source into the serine, a manufacturing process of separating the D-serine and the L-serine can be omitted in the method of the present disclosure.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A method for converting a carbon source into serine, comprising:

synthesizing a DNA sequence;

implanting the DNA sequence into a plasmid, so that the plasmid includes gene sequences of SEQ ID NO: 1, SEQ ID NO: 2, and SEQ ID NO: 3;

implanting the plasmid into cyanobacteria through an electroporation treatment, so as to obtain modified cyanobacteria; and providing the carbon source to the modified cyanobacteria, so that the modified cyanobacteria convert the carbon source into the serine.

2. The method according to claim 1, wherein the plasmid is an *Escherichia coli* plasmid.

3. The method according to claim 1, further comprising: implanting the plasmid into *Escherichia coli* for mass production.

4. The method according to claim 1, wherein the cyanobacteria are *Synechococcus elongates.*

5. The method according to claim 1, wherein the modified cyanobacteria are capable of producing 3-phosphoglycerate dehydrogenase, phosphoserine phosphatase, and phosphoserine aminotransferase.

6. The method according to claim 1, wherein the electroporation treatment comprises subjecting the cyanobacteria to a voltage between 0.5 kV and 1.5 kV for 2 msec to 10 msec.

7. The method according to claim 1, wherein the serine is L-serine.

8. The method according to claim 1, wherein the carbon source is carbon dioxide, glucose, sucrose, fructose, or galactose.

9. A method for converting a carbon source into serine, comprising:

providing a carbon source to modified cyanobacteria, so that the modified cyanobacteria convert the carbon source into the serine;

wherein the modified cyanobacteria include gene sequences of SEQ ID NO: 1, SEQ ID NO: 2, and SEQ ID NO: 3.

10. The method according to claim 9, wherein the serine is L-serine.

11. The method according to claim 9, wherein the carbon source is carbon dioxide, glucose, sucrose, fructose, or galactose.

12. The method according to claim 9, wherein the modified cyanobacteria convert the carbon source into glyceraldehyde 3-phosphate (G3P), and are capable of producing 3-phosphoglycerate dehydrogenase (SerA), so as to convert the glyceraldehyde 3-phosphate (G3P) into 3-phosphohydroxypyruvate (3P-HP).

13. The method according to claim 12, wherein the modified cyanobacteria are capable of producing phosphoserine aminotransferase (SerC), so as to convert the 3-phosphohydroxypyruvate (3P-HP) into 3-phosphoserine (3P-serine).

14. The method according to claim 13, wherein the modified cyanobacteria are capable of producing phosphoserine phosphatase (SerB), so as to convert the 3-phosphoserine (3P-serine) into the serine.

* * * * *

SEQUENCE LISTING

```
Sequence total quantity: 3
SEQ ID NO: 1            moltype = DNA  length = 1590
FEATURE                 Location/Qualifiers
source                  1..1590
                        mol_type = genomic DNA
                        organism = Synechococcus elongatus
SEQUENCE: 1
atgcccaagg tcttggtgtc cgatccaatc gatcaggttg gtcttgatat cctctcgcaa  60
gtggcccaag tggatgtcaa aaccggcctg agtcctagtg agctagcgca aatcataggt  120
gaatatgacg ccctgatgct gcgcagcggg acacgtgtca cggccgaagt gatcgaagcc  180
ggccaaaaac tgcgtattat tggtcgggct ggggttggtg ttgacaatgt tgatgtcccg  240
gcggctaccc gccggggaat tgtggtcgtc aatagcccag aaggcaatac tatcgccgcg  300
gcagagcaca cactcgcaat gatgttgtcg ctgagccgcc acattccgga tgccaatgct  360
tccactaaga gtggtggctg ggatcgcaag tcttttgtcg gcactgaggt ctacaaaaaa  420
accctggggg ttgttggtct tggcaaaatc ggaagccacg tcgcgacggt cgcgaaggcg  480
atgggcatga aactcctggc ctacgacccc tttatttcag cagaacgagc ggaacagatt  540
ggggcccggt tggtcgagtt ggatattctc tttcaggaag cagactacat cacgctgcat  600
attcccaaaa cccccgaaac cgccaacctg atcaatgctg aaaccctagc caagatgaag  660
cccaccactc gcattatcaa ctgcgcccgt ggaggggtca tcaacgaaca agcacttgcg  720
gatgcgatcg ctgctggcaa aatcggcggt gcggccctgg atgtttacga tcaagagccc  780
ctccaggctg attcaccgct gcgagcactg ggtaagaacc tgatcttgac gccccatcta  840
ggtgcctcca caaccgaggc acaggtcaac gtcgcagtag acgtagcgga gcagattcgg  900
gacgtcctcc tgggcctccc agcccggagt gccgtgaaca tccctgggct ctatcctgat  960
attttggaaa agctgcggcc gtatctgcag ttggcggaaa ctctgggcaa cctccttagt  1020
caagtcgcgg gcggccgcct cgagcaactc acggttcgat tgcaaggcga gttggctgcc  1080
cagcaatctc agccgatcgt ggtggctgct ttaaaaggcc tattgaccca agcattacga  1140
gaacgtgtta actatgtcaa tgctatgatc gaggccaaag agcgcggaat tcgcatcatc  1200
gaaacacgcg atgagagcgt gcgcgatgac tatgccgggg ggtccttgca gctggttgcc  1260
```

-continued

```
acgggcagca atggtgaaca tcgtgtgatg ggcgctctgt tgggcgatgg cgagattcgg  1320
attaccaatg tggacgaatt ccctgtgaac gtcccgccca gccgatacat gctgttcacg  1380
cggcaccgcg acatgccggg catcattgga aaaattgggt cgctcttggg ttctttcaac  1440
gtgaatattg cctcgatgca ggttggacgc cgcattgtgc gcggtgacgc ggtgatggtg  1500
ctgtcgctcg atgatccgtt accagaagga atcctagcgg aaattacgaa ggtggctggc  1560
atcagcgatg cttacaccgt tgtgctctaa                                  1590

SEQ ID NO: 2           moltype = DNA  length = 1338
FEATURE                Location/Qualifiers
source                 1..1338
                       mol_type = genomic DNA
                       organism = Synechococcus elongatus
SEQUENCE: 2
atggcaacac gtgtcgtctt agtgcgtcat gggcaaagca gctacaacgc cgctggtcgg  60
atccaaggac gttgcgataa ctcgcaactg actgatcgag gcgcagcgga cgcagtcaaa  120
gttgcagctg cactgaatgg cattcccttc gctgctgcct actgctcacc actgcagcga  180
gccaaacgga cggcagaaat catcattgag cagatcgaaa cgccgccagc tttggcggtg  240
agcgatggcc ttctcgaagt cgacctgccg ctgtgggagg gcctcagtcg cgaagaagtg  300
cgctctcagt acgccgaact ctatcgccag tggcacgaag ccccccatga gctagtcctg  360
accgtgccgg acggtcaagg tggcagccgc gagcatgccc ctgttttggc tctgtttgag  420
caagcgcggc agttttggaa ggatttgttg gaacggcatc gcgatcaaac tgtactactg  480
gttgcccaca acgggattct gcgctcactg atcgcgacgg cattgggcgt tgatcctagc  540
gcctatcaag tgatccgaca atctaactgc gggatcagtg tgctcaactt cgcagatgga  600
accaatcagc cggcccagct ggaatgtcta aatctaaccg caccgcttgg cgatgccctc  660
cctgatcgcg gcgcttcgtc gggcgtccga cttctgctgg ttcgccatgg tgaaaccgac  720
tggaatcgcc aaaaacgatt ccaagggcaa atcgatattc cgctgaatga caacggtagg  780
gctcaggcgc gtagtgcggc cgaatttttg gcgcccattc agattgactt tgcggtctcc  840
tcgccgatgg cgcggccgaa ggaaacggct gagctgattt tggagcgcca ccccaattgt  900
gaactgtcgg tggacgatcg cctccaagaa attggtcacg gcctctggga gggaaagctc  960
gaggaagaga tcgcagcgga attcggcgaa ttgttacagc tctggaaaga tcagcccgaa  1020
caggtgcaga tgcccgaggg ggagaacctg caagaggttt gggatcgcag cgtcgcggct  1080
tgggaagcga tcgtcgccaa tgccccagaa ggcagtaccg gcttagtggt cgctcacgat  1140
gcggtcaaca aagtgattct atgccacgtc ttgggcttgt cccccgccga catttggagc  1200
atcaagcagg gcaacggggc tgttacagtg gttgactatc ccaagcggct cgattcccgt  1260
ccagtactcc aagccatgaa tctgactctg catctcgatg gtgccgtgtt ggatcgcacc  1320
gccgcgggtg ctctttaa                                               1338

SEQ ID NO: 3           moltype = DNA  length = 1080
FEATURE                Location/Qualifiers
source                 1..1080
                       mol_type = genomic DNA
                       organism = Synechococcus euryphyces
SEQUENCE: 3
atgatgggca atcgcgtata caacttcaac gcaggacctt ctgcgatgcc gctgcccgtg  60
ttagaggaaa ttcagcagga gtttctagac tttaatcaca cgggcatgag catcgtggaa  120
atcagccatc gatcggatgc atatcaaaag atgcaggatg aaacgattgc gctccttcat  180
aagttattga atattcccga cgagtacggc attaccttca tgcaaggcgg tggttcgatg  240
cagttcctga tgcatggcgc taattttttg aagcaccgcg gggctacat caatactggt  300
gtctggagta aaaaagccaa agagggtgcg gctttttatg gcgatgtcta cgacgttgct  360
acgagtgagg gcgaaggttt tcggcggatt ccgggcccag aggaattcga tctgctgcct  420
gataccgact acgtctatct gaccagcaac aacactattc acggcacaca gtggcaagcc  480
ttcccccaca tcgatctccc gctaatatgc gatatgtcga gtgattttct ttcgcggcct  540
gtggatgtga agaactttga cttcatctat gctgggattc aaaaaaatgt tggaccagcg  600
ggggcagtga ttggtatcgc aaagcattca tacctggaaa cagcccgtca agacctgccg  660
atcatgctgc agtacaaaac ctttttttgat cacgacagta cttataacac gccgcccgtt  720
ttttgcatct acttcgtcaa caaggtgttg cactggctcg atgagcgagg ggggctcaag  780
gagactgagc ggatcaacaa agaaaaggcg gcgtttgtct acgatgcgat cgatgccagc  840
gatggcttct atcgccccca tgccgccaag gattcacgca gcttgatgaa catcaccttc  900
aatctggtga cgccagaact cgagaaagaa tttgtttccc gtgcagccga agaaaaactg  960
attggtctca aaggtcatcg ttctattggc ggctgtcgcg cttccaccta taatgctgtc  1020
accaaagaag cctgtgaacg cttggccgac tttatgcacc gcttccgcaa agttcattaa  1080
```